United States Patent [19]

Chan et al.

[11] Patent Number: 4,642,346

[45] Date of Patent: Feb. 10, 1987

[54] ANHYDROUS CRYSTALLINE 9-(1,3-DIHYDROXY-2-PROPOXYMETHYL)-GUANINE

[75] Inventors: Tai W. Chan, Palo Alto; Huong T. Nguyen, Saratoga, both of Calif.

[73] Assignee: Syntex (U.S.A.) Inc., Palo Alto, Calif.

[21] Appl. No.: 747,631

[22] Filed: Jun. 24, 1985

[51] Int. Cl.⁴ .................... C07D 473/02; A61K 31/52
[52] U.S. Cl. ..................................... 544/276; 544/277
[58] Field of Search ................ 544/276, 277; 514/262

[56] References Cited

U.S. PATENT DOCUMENTS

| | | | |
|---|---|---|---|
| 4,199,574 | 4/1980 | Schaeffer et al. | 544/276 |
| 4,355,032 | 10/1982 | Verheyden et al. | 544/276 |
| 4,556,659 | 12/1985 | Verheyden et al. | 544/276 |
| 4,579,849 | 4/1986 | MacCoss et al. | 514/262 |

Primary Examiner—Nicholas S. Rizzo
Attorney, Agent, or Firm—Annette M. Moore; Tom M. Moran

[57] ABSTRACT

Novel anhydrous crystalline 9-(1,3-dihydroxy-2-propoxymethyl)guanine useful as an antiviral agent.

13 Claims, 6 Drawing Figures

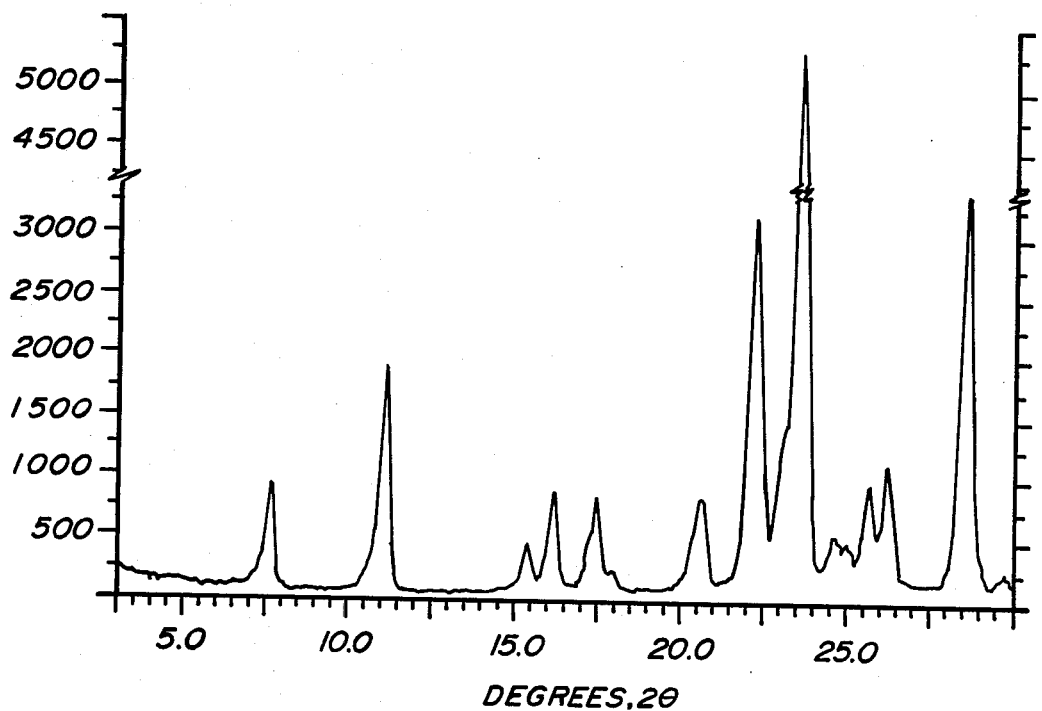
FIG. IA
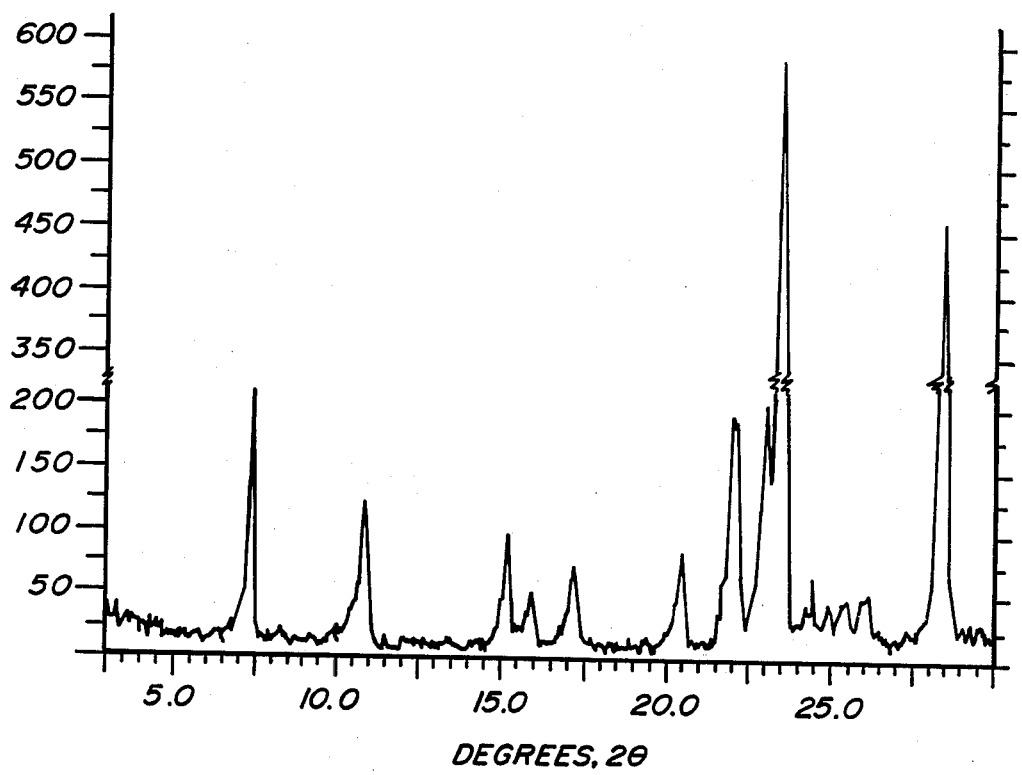
FIG. IB

FIG. IC
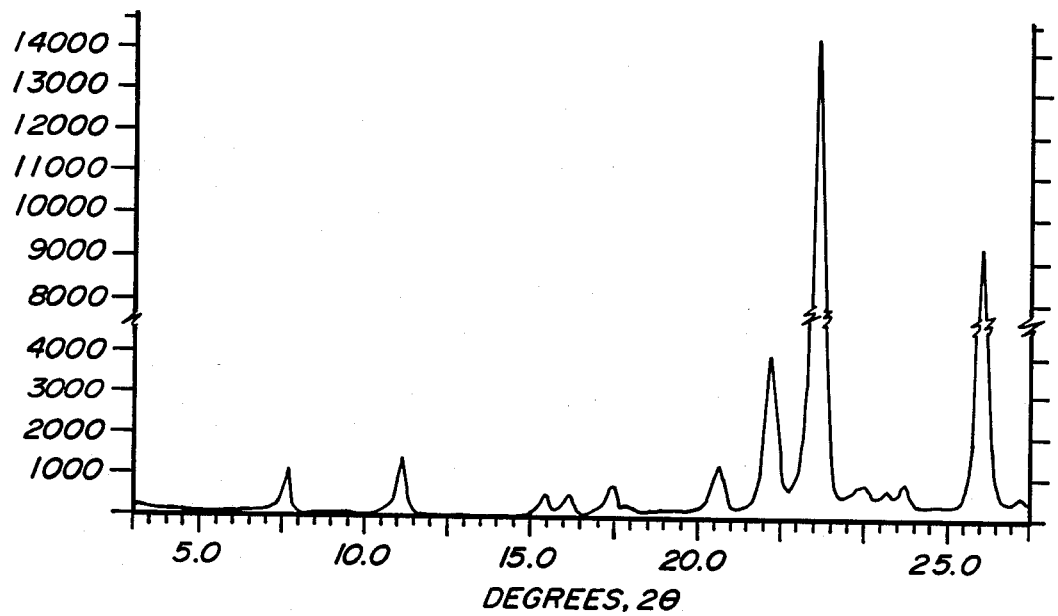
FIG. ID
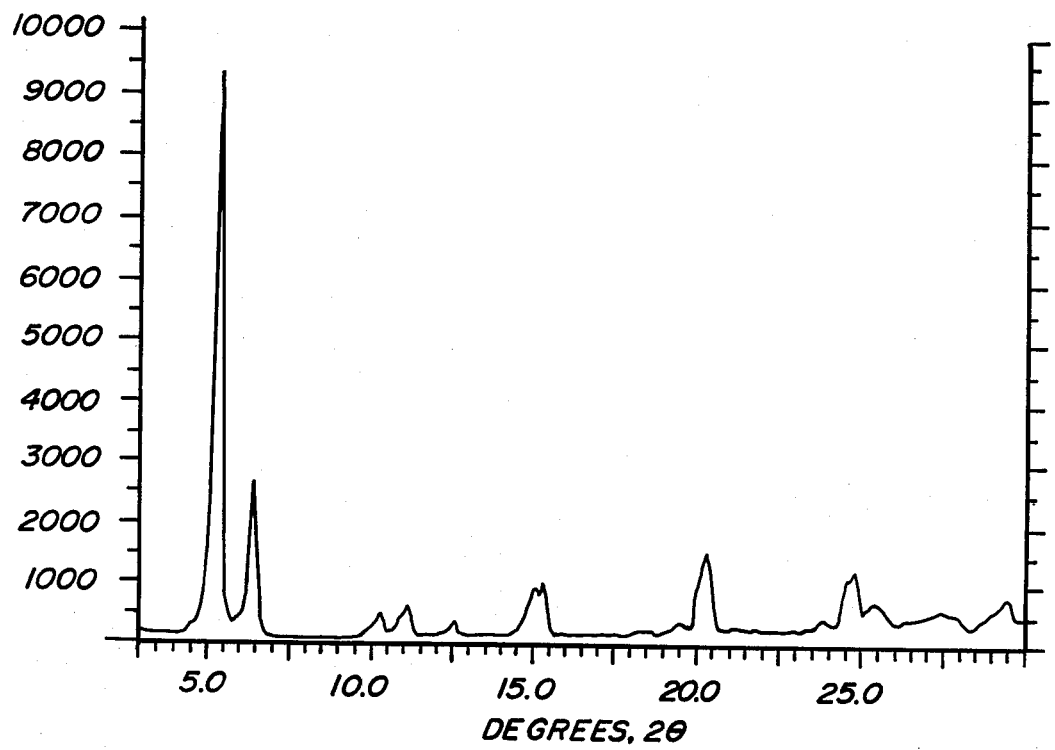

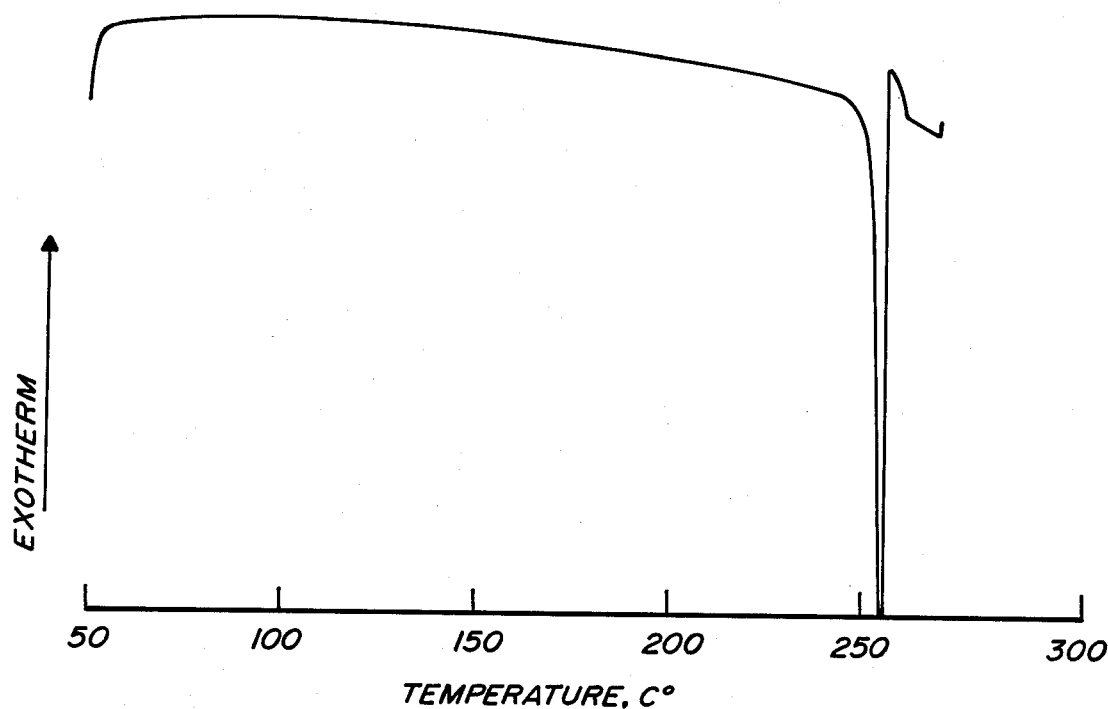
FIG. IIA
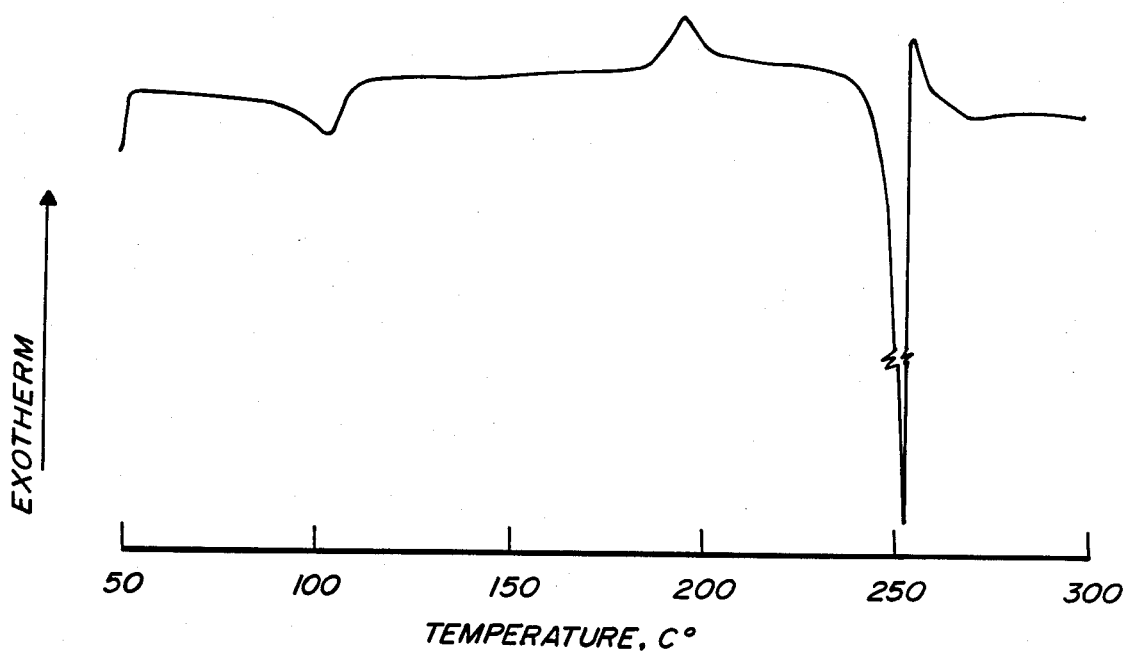
FIG. IIB

ANHYDROUS CRYSTALLINE 9-(1,3-DIHYDROXY-2-PROPOXYMETHYL)GUANINE

BACKGROUND OF THE INVENTION

1. Field of the Invention

This invention relates to novel anhydrous crystalline 9-(1,3-dihydroxy-2-propoxymethyl)guanine. The invention also relates to a process for preparing the novel crystalline form.

2. Related Disclosure

The compound 9-(1,3-dihydroxy-2-propoxymethyl)-guanine also known as DHPG is a very potent antiviral agent. (See U.S. Pat. No. 4,355,032.) DHPG is known to exist as an unstable hydrate. This hydrate has serious disadvantages because it is hygroscopic at ambient humidity. The hygroscopic nature of DHPG hydrate causes handling and formulating problems.

Surprisingly, there has been discovered an extremely stable anhydrous crystalline DHPG which is unusually resistent to water absorption. This unusually stable form has better physical characteristics than the known DHPG hydrate. Because of its non-hygroscopic nature anhydrous crystalline DHPG retains a better physical appearance over a longer period of time. Any improvement in the physical appearance of a dosage form of a drug, of course, enhances both physician and patient acceptance and increases the likelihood of success of the treatment.

The resistance to water absorption results in reproducible batches of highly pure DHPG. Because of the high purity and extreme stability of anhydrous crystalline DHPG it is better suited to be used as a reference standard in HPLC analysis.

SUMMARY OF THE INVENTION

The first aspect of this invention is novel anhydrous crystalline DHPG.

The second aspect of this invention is a process for preparing novel anhydrous crystalline DHPG which comprises dissolving a suitable form of DHPG in an appropriate solvent system such as an oxygen-containing solvent system maintained at an elevated temperature, cooling the solution and recovering novel anhydrous crystalline DHPG.

The third aspect of this invention is a process for preparing novel anhydrous cyrstalline DHPG by heating DHPG hydrate until the anhydrous crystalline DHPG forms.

DETAILED DESCRIPTION AND PREFERRED EMBODIMENTS CHARACTERIZATION

The broadest aspect of the present invention is novel anhydrous crystalline 9-(1,3-dihydroxy-2-propoxymethyl)guanine. This crystalline DHPG is characterized by a melting point of 243°-245° C., water of hydration of less than 1% by weight and the powder X-ray diffraction pattern shown in FIGS. IA and IB.

The compound of this invention is best characterized by the X-ray powder diffraction pattern determined in accordance with procedures which are known in the art. For a discussion of these techniques see J. Haleblian, *J. Pharm. Sci.* 64, 1269–1288, 1975 and J. Haleblain, W. McCrone, *J. Pharm. Sci.*, 58, 911–929, 1969. Although the X-ray powder diffraction patterns of anhydrous crystalline DHPG made by different routes may vary slightly in intensity, the peaks are at the same $2\theta$ values and thus represent the same crystalline structure. For example, FIGS. IA and IB each show the X-ray pattern for anhydrous crystalline DHPG prepared by two different routes.

Physically, the anhydrous crystals of this invention are obtained as a white powder consisting of aggregates of birefringent rod-like or needle-like crystals. These crystals are much less hygroscopic than other crystalline forms of DHPG such as DHPG hydrate.

As used herein the term "anhydrous" refers to a crystalline form which contains less than 1% water of hydration. The term "lower alcohols" refers to ROH wherein R is a branched or unbranched alkyl group of one to four carbon atoms.

An appropriate solvent is any solvent which is capable of dissolving DHPG. Such solvents which are useful in the present invention are organic non-oxygen containing solvents such as acetonitrile, benzene and the like, and oxygen-containing solvents.

An oxygen-containing solvent as used herein refers to a solvent which is capable of dissolving DHPG and contains oxygen as part of its molecular structure. An organic oxygen-containing solvent has no more than four carbon atoms in its structure. The inorganic oxygen-containing solvent which is useful in this invention is water. Examples of organic oxygen-containing solvents are dimethyl acetamide, acetone, and lower alcohols such as methanol, ethanol, 1-propanol, 2-propanol and butanol.

The term "mixture" as used herein refers to solutions and to suspensions.

"The term "suitable form of DHPG" refers to any form of DHPG which may be converted to the anhydrous crystalline DHPG of the invention.

PREPARATION

The above crystalline form of DHPG is prepared by dissolving a suitable form of DHPG in a oxygen-containing solvent system such as dimethyl acetamide or water combined with methanol or acetone. Other oxygen-containing solvents which are useful in the present invention are lower alcohols either singly or in combination. The anhydrous DHPG may also be prepared by heating a suitable form of DHPG such as DHPG hydrate.

One preferred embodiment of the instant invention is the process for preparing anhydrous DHPG using a solvent system of lower alcohols either singly or in combination.

Novel anhydrous crystalline DHPG is prepared by dissolving or suspending 50 to 500 mg of a suitable form of DHPG such as DHPG hydrate in an oxygen-containing solvent at an elevated temperature for a time sufficient for the anhydrous crystals of DHPG to form.

When the oxygen-containing solvent is dimethyl acetamide or water a sufficient amount, i.e., 50–250 mg of DHPG is dissolved with stirring in 2.5 to 15 ml of the solvent heated to a temperature of 60° to 100° C. to form a saturated system. To this hot solution is added two to five times the volume of methanol or acetone. After 5 to 30 minutes the solution is cooled to room temperature and the crystals which form are recovered by filtration and then air-dried.

When the oxygen-containing solvent is an alcohol of one to four carbon atoms, preferably one to three carbon atoms, 100 to 400 mg of a suitable form of DHPG is suspended in 1 to 4 ml of the alcohol heated to 40° to 80° C. for 15 minutes to 2 hours, preferably for 30 minutes to 1-½ hours. The mixture is cooled to room temperature and the crystals which form are recovered by filtration and air-dried. Preferred alcohols are methanol, ethanol, 1-propanol, 2-propanol and alcohol solvent systems such as 2-propanol/ethanol.

Another method for preparing anhydrous crystalline DHPG is by heating a suitable form of DHPG such as DHPG hydrate to 200°–220° C., preferably to 210° C. for 5 to 60 minutes, preferably for 5 to 30 minutes.

DHPG is prepared by the method described in U.S. Pat. No. 4,355,032 incorporated herein by reference.

The following specific description is given to enable those skilled in the art to more clearly understand and practice the invention. It should not be considered as a limitation upon the scope of the invention but merely as being illustrative and representative thereof.

PREPARATION A

DHPG hydrate is prepared by the method described in U.S. Pat. No. 4,355,032 with crystallization from water.

EXAMPLE 1

Eighty mg of 9-(1,3-dihydroxy-2-propoxymethyl)-guanine prepared in Preparation A was dissolved in 3.5 ml of dimethyl acetamide at 70° C. To the hot solution, 8 ml of methanol was added and the solution turned cloudy immediately. On cooling, the crystals which form were recovered by filtration and washed with 10 ml of methanol and air-dried to give anhydrous 9-(1,3-dihydroxy-2-propoxymethyl)guanine, m.p. 243°–245° C.

EXAMPLE 2

To a solution of 200 mg of 9-(1,3-dihydroxy-2-propoxymethyl)guanine prepared in Preparation A in 10 ml water at 70° C. was added approximately five times the volume of methanol. The crystals that appeared slowly (one to two hours) were recovered by filtration and air-dried to give anhydrous 9-(1,3-dihydroxy-2-propoxymethyl)guanine, m.p. 243°–245° C.

EXAMPLE 3

Three hundred mg of DHPG prepared in Preparation A were suspended in 2 ml of 2-propanol at 60° C. for 1 hour. Crystals of anhydrous 9-(1,3-dihydroxy-2-propoxymethyl)guanine were recovered by filtration and were air-dried, m.p. 243°–245° C.

EXAMPLE 4

One hundred mg of 9-(1,3-dihydroxy-2-propoxymethyl)guanine prepared in Preparation A was heated in an oven at 200°–220° C. for 10 minutes and then cooled to room temperature. The anhydrous crystals of 9-(1,3-dihydroxy-2-propoxymethyl)guanine which were formed had m.p. 243°–245° C.

EXAMPLE 5

X-ray powder diffraction patterns of samples of the material obtained from Preparation A (DHPG hydrate), Example 1, Example 3 and Example 4 were determined on a Nicolet X-ray diffractometer with a fine focus tube and a diffracted beam monochrometer. The scanning angle was from 5° to 30° $2\theta$, at 2° per minute. FIG. I shows the X-ray diffraction patterns of (A) anhydrous crystalline DHPG obtained in accordance with Example 1 (FIG. IA), (B) anhydrous crystalline DHPG obtained in accordance with Example 3 (FIG. IB), (C) anhydrous crystalline DHPG obtained in accordance to Example 4 and (D) DHPG hydrate obtained in accordance with Preparation A (FIG. ID).

It is apparent that the X-ray diffraction patterns in FIGS. IA, IB and IC are very similar with the highest peaks occurring at 23°–25°$2\theta$ whereas the X-ray diffraction pattern in FIG. ID is different from the diffraction pattern in FIGS. IA, IB and IC with the highest peak in FIG. ID occurring at 5°$2\theta$. The Figures show that the crystalline form of DHPG prepared in Examples 1, 3 and 4 is different from the crystalline form prepared in Preparation A.

EXAMPLE 6

This example describes a method for distinguishing DHPG hydrate from anhydrous crystalline DHPG using differential scanning calorimetry (DSC). The instrument used was a Perkin-Elmer DSC-2. The heating rate was 10° C. per minute, and the sensitivity range was 5 mcal per second.

The DSC thermogram for anhydrous crystalline DHPG (FIG. IIA) shows no phase transitions until melting at 242° C. to 255° C.

On the other hand, the DSC thermogram for DHPG hydrate (FIG. IIB) shows an endotherm at 97° C. and an exotherm starting at 185° C. and a melting endotherm at 246° C.

EXAMPLE 7

The hydroscopicity of anhydrous crystalline DHPG and DHPG hydrate at different relative humidities is depicted below. A small amount of the compound (~10 mg) in a weighing bottle was weighed and placed in a chamber with a controlled relative humidity. The sample was weighed again at various time intervals and the percentage of water absorbed was calculated.

TABLE

| Crystalline Form | Relative Humidity, % | Time, Days | Weight Change, % |
|---|---|---|---|
| Anhydrous DHPG | 47 | 2 | −0.05 |
|  |  | 7 | 0.09 |
|  | 76 | 2 | 0.26 |
|  |  | 7 | 0.40 |
|  | 81 | 2 | 0.56 |
|  |  | 7 | 0.70 |
|  |  | 10 | 0.56 |
|  | 93 | 2 | 17.25 |
|  |  | 7 | 17.34 |
| DHPG Hydrate | 47 | 2 | 0.26 |
|  |  | 7 | 0.47 |
|  | 76 | 2 | 6.02 |
|  |  | 7 | 6.40 |
|  | 81 | 2 | 6.93 |
|  |  | 7 | 7.46 |
|  |  | 10 | 7.23 |

The above table depicting the % weight change at various relative humidities shows that anhydrous crystalline DHPG of the invention is extremely stable and non-hydroscopic at 81% relative humidity for an extended period of time while the hydrate absorbed a significant amount of water at 76% relative humidity after only 2 days. The unusual stability of the anhydrous crystalline DHPG results in highly reproducible batches and better storage charcteristics.

What is claimed is:

1. Anhydrous crystalline 9-(1,3-dihydroxy-2-propoxymethyl)guanine.

2. The anhydrous crystals of claim 1 further characterized by water of hydration of less than 1% w/w.

3. The anhydrous crystals of claim 2 further characterized by m.p. 243° C.–245° C.

4. The anhydrous crystals of claim 3 characterized by the powder X-ray diffraction pattern shown in FIGS. IA, IB or IC.

5. The process for preparing the anhydrous crystals of claim 1 which comprises
   (i) adding 9-(1,3-dihydroxy-2-propoxymethyl)guanine to a heated oxygen-containing solvent;
   (ii) cooling the mixxture formed in step (i) to room temperature; and
   (iii) recovering the crystals formed in step (ii).

6. The process of claim 5 wherein the oxygen-containing solvent is dimethyl acetamide or water.

7. The process of claim 6 wherein the solvent is warmed to 60° to 100° C.

8. The process of claim 7 which further comprises adding methanol or acetone to the warm solution.

9. The process of claim 5 wherein the oxygen-containing solvent is an alcohol of one to four carbon atoms.

10. The process of claim 9 wherein the solvent is warmed to 40° to 80° C.

11. A process for preparing the anhydrous crystals of claim 1 which comprises heating a suitable form of 9-(1,3-dihydroxy-2-propoxymethyl)guanine.

12. The process of claim 11 wherein the suitable form is 9-(1,3-dihydroxy-2-propoxymethyl)guanine hydrate.

13. The process of claim 12 wherein the hydrate is heated to 200°–220° C.

* * * * *